(12) United States Patent
Okuno et al.

(10) Patent No.: US 10,585,033 B2
(45) Date of Patent: Mar. 10, 2020

(54) MICROPARTICLE MEASURING DEVICE AND MICROPARTICLE ANALYSIS METHOD

(71) Applicant: Sumitomo Electric Industries, Ltd., Osaka-shi (JP)

(72) Inventors: Takuya Okuno, Yokohama (JP); Akinori Kimura, Yokohama (JP); Ichiro Sogawa, Yokohama (JP); Hiroshi Suganuma, Yokohama (JP)

(73) Assignee: Sumitomo Electric Industries, Ltd., Osaka-shi (JP)

( * ) Notice: Subject to any disclaimer, the term of this patent is extended or adjusted under 35 U.S.C. 154(b) by 0 days.

(21) Appl. No.: 16/213,424

(22) Filed: Dec. 7, 2018

(65) Prior Publication Data

US 2019/0107479 A1    Apr. 11, 2019

Related U.S. Application Data

(63) Continuation of application No. PCT/JP2017/019544, filed on May 25, 2017.

(30) Foreign Application Priority Data

Jun. 9, 2016    (JP) ................................ 2016-115568

(51) Int. Cl.
*G06T 7/62* (2017.01)
*G01N 15/14* (2006.01)
(Continued)

(52) U.S. Cl.
CPC ....... *G01N 15/1463* (2013.01); *G01N 15/147* (2013.01); *G01N 15/1429* (2013.01);
(Continued)

(58) Field of Classification Search
None
See application file for complete search history.

(56) References Cited

U.S. PATENT DOCUMENTS

| 4,999,513 A | 3/1991 | Ito et al. | |
|---|---|---|---|
| 2014/0273067 A1* | 9/2014 | Wanders | ............ G01N 15/1468 435/29 |

(Continued)

FOREIGN PATENT DOCUMENTS

| JP | H01-296136 A | 11/1989 |
|---|---|---|
| JP | H10-115612 A | 5/1998 |
| JP | H11-258144 A | 9/1999 |
| JP | 2001-255260 A | 9/2001 |
| JP | 2001-272328 A | 10/2001 |
| JP | 2010-085194 A | 4/2010 |

(Continued)

OTHER PUBLICATIONS

Xiaozhen "In-situ particle measurement with blurred image processing using telecentric lenses" (Year: 2012).*

*Primary Examiner* — Eileen M Adams
(74) *Attorney, Agent, or Firm* — Baker Botts L.L.P.; Michael A. Sartori

(57) ABSTRACT

There are provided a microparticle measuring device capable of analyzing microparticles with increased accuracy and a microparticle analysis method. According to a microparticle measuring device 1, transmission images of microparticles in the liquid sample are captured by a plurality of image capturing units that are disposed in mutually different orientations with respect to a liquid feed pipe when viewed in a cross section orthogonal to the flowing direction of a liquid sample in the liquid feed pipe, and the microparticles are analyzed by an analyzing unit on the basis of the transmission images.

13 Claims, 3 Drawing Sheets

(51) Int. Cl.
  *G01N 33/48* (2006.01)
  *G01N 21/49* (2006.01)
  *G01N 21/27* (2006.01)
  *H04N 5/225* (2006.01)
  *H04N 5/247* (2006.01)
  *G01N 15/10* (2006.01)

(52) U.S. Cl.
  CPC ......... *G01N 15/1434* (2013.01); *G01N 21/27* (2013.01); *G01N 21/49* (2013.01); *G01N 33/48* (2013.01); *G06T 7/62* (2017.01); *H04N 5/2256* (2013.01); *H04N 5/247* (2013.01); *G01N 2015/1006* (2013.01); *G01N 2015/1445* (2013.01); *G01N 2015/1497* (2013.01)

(56) References Cited

U.S. PATENT DOCUMENTS

| | | |
|---|---|---|
| 2015/0111218 A1 | 4/2015 | Tateno et al. |
| 2015/0293009 A1* | 10/2015 | Henning ............ G01N 15/1463 356/72 |
| 2016/0109372 A1* | 4/2016 | Wanders ............ G01N 15/1425 356/40 |
| 2019/0033209 A1* | 1/2019 | Kluckner ................ G01N 35/04 |

FOREIGN PATENT DOCUMENTS

| | | |
|---|---|---|
| WO | 02/080090 A1 | 10/2002 |
| WO | 03/019141 A2 | 3/2003 |
| WO | 2012/142496 A1 | 10/2012 |
| WO | 2013/128914 A1 | 9/2013 |

* cited by examiner

MICROPARTICLE MEASURING DEVICE AND MICROPARTICLE ANALYSIS METHOD

CROSS-REFERENCE TO RELATED APPLICATION

This is a continuation application of PCT/JP2017/019544 claiming the benefit of the Japanese Patent Application No. 2016-115568 filed on Jun. 9, 2016, which is incorporated by reference herein in its entirety.

TECHNICAL FIELD

The present invention relates to a microparticle measuring device and a microparticle analysis method using the device.

BACKGROUND ART

It is known that, before analysis of microparticles such as cells, pretreatment that enables the target microparticles to be distinguishable is performed. For example, WO 03/019141 describes a method of bonding labeled samples to target cells and using labels thereof to identify the target cells.

SUMMARY OF INVENTION

Technical Problem

The present invention provides a microparticle measuring device capable of analyzing microparticles with increased accuracy and a microparticle analysis method using the device.

Solution to Problem

A microparticle measuring device of the present invention includes a liquid feed pipe that has light transmittance and that has an inner portion configured such that through the inner portion, a liquid sample containing microparticles flows; a plurality of image capturing units that are disposed in mutually different orientations with respect to the liquid feed pipe when viewed in a cross section orthogonal to a flowing direction of the liquid sample in the liquid feed pipe and that are configured to capture transmission images of the microparticles contained in the liquid sample that moves in the liquid feed pipe; and an analyzing unit that is configured to analyze the microparticles based on the transmission images of the microparticles captured by the image capturing units.

The microparticle measuring device of the present invention may further include a plurality of light source units that are each disposed in an orientation facing a corresponding one of the plurality of image capturing units with the liquid feed pipe therebetween and that are configured to emit measurement light toward the liquid feed pipe. In addition, the microparticle measuring device may further include a position adjusting mechanism capable of adjusting a distance between an image capturing unit included in the plurality of image capturing units and the liquid feed pipe. In the microparticle measuring device of the present invention, two image capturing units of the plurality of image capturing units are preferably disposed such that directions of image capturing thereof are orthogonal to each other when viewed in the cross section orthogonal to the flowing direction of the liquid sample in the liquid feed pipe.

In the microparticle measuring device of the present invention, the plurality of image capturing units may be disposed so as to capture transmission images at an identical position in a flowing direction of the liquid sample in the liquid feed pipe and are configured to acquire information on shapes of the microparticles. Moreover, the plurality of image capturing units may be disposed so as to capture transmission images at an identical position in the flowing direction of the liquid sample in the liquid feed pipe and are configured to acquire information on outer shapes of the microparticles, and the analyzing unit may be configured to estimate volumes of the microparticles based on the transmission images of the microparticles captured by the image capturing units. In addition, the plurality of image capturing units may be disposed so as to capture transmission images at an identical position in the flowing direction of the liquid sample in the liquid feed pipe and are configured to acquire information on the shapes of the microparticles, and the analyzing unit may identify, based on the transmission images of the microparticles captured by the image capturing units, the microparticles by using a statistical technique, machine learning, or pattern recognition. Further, in the microparticle measuring device of the present invention, the analyzing unit may be configured to estimate, based on the transmission images of the microparticles captured by the image capturing units, the number of the microparticles contained in the liquid sample.

As another form of the present invention, in a microparticle analysis method of the present invention using the microparticle measuring device of the present invention, the analyzing unit is configured to determine whether the microparticles contained in the liquid sample are cells of a specific type. In addition, in a microparticle analysis method of the present invention using the microparticle measuring device of the present invention, the analyzing unit is configured to evaluate differentiation degrees of cells, which are the microparticles contained in the liquid sample.

Advantageous Effects of Invention

According to the microparticle measuring device of the present invention, it becomes possible to analyze microparticles with increased accuracy and without bonding of labeled samples, by capturing transmission images of the microparticles in a plurality of directions and using the transmission images for the analysis.

DESCRIPTION OF EMBODIMENTS

Specific examples of a microparticle measuring device according to the present invention will be described below with reference to the drawings. Note that the present invention is not limited to these presented examples; the present invention is indicated by the claims and intends to include all modifications within the meaning and scope equivalent to the claims.

Performing pretreatment such as bonding labeled samples to target microparticles results in a subsequent analysis to be performed by using the microparticles to which the labeled samples are bonded. In addition, there is a possibility that the pretreatment damages the microparticles. Thus, analysis of microparticles subjected to pretreatment is considered to have room for improvement in terms of accuracy of information acquired by analyzing the microparticles.

Figure 1:
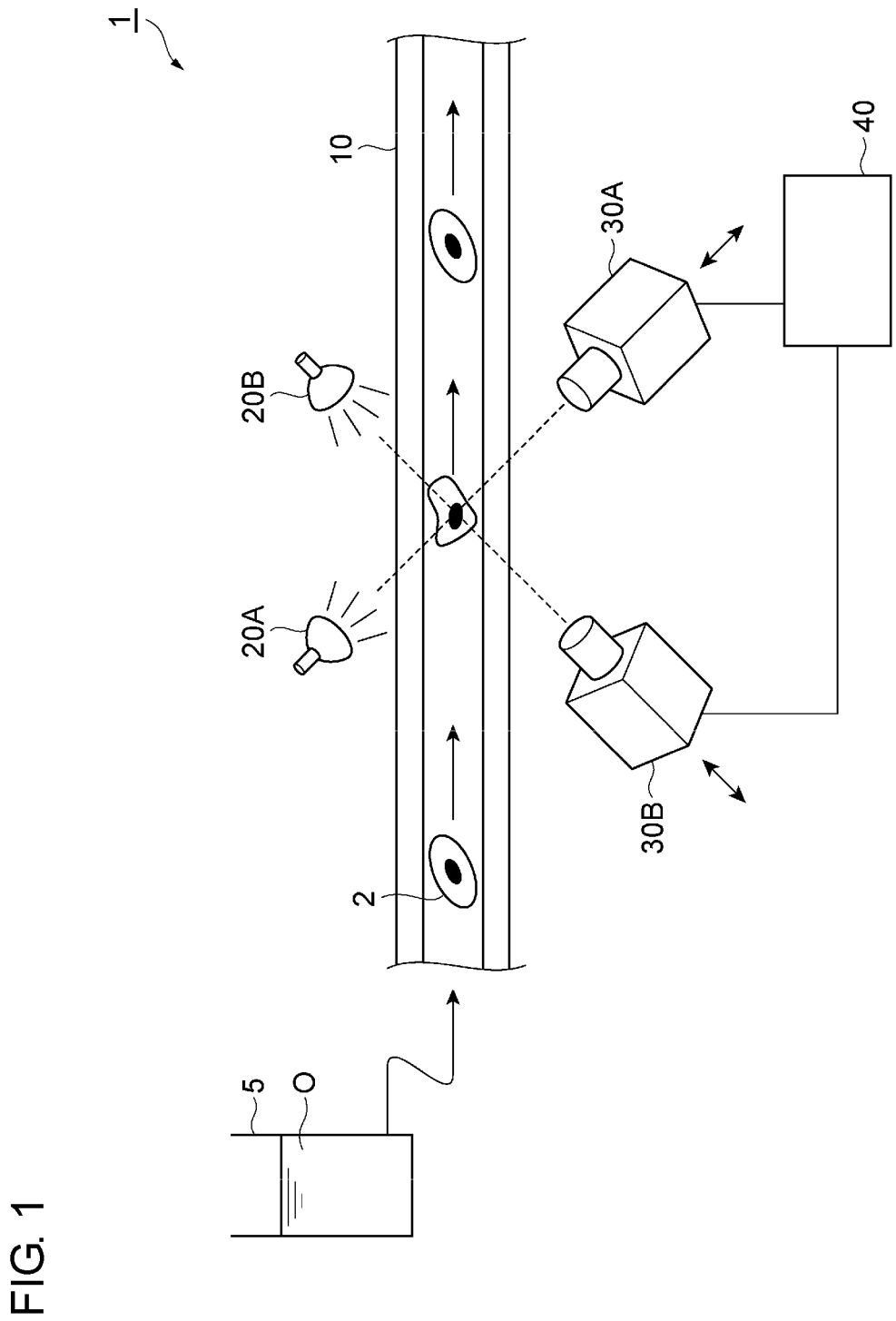
FIG. 1 is a conceptual diagram of a microparticle measuring device according to an embodiment of the present invention.

FIG. 1 is a conceptual diagram of a microparticle measuring device 1 according an embodiment of the present invention. The microparticle measuring device 1 is a device that measures microparticles dispersed in a liquid. Combination of microparticles and a liquid in which the microparticles are dispersed is not particularly limited; for example, the microparticles may be cells, and the liquid in which the microparticles are dispersed may be blood or a liquid derived from blood.

In the microparticle measuring device 1, a liquid sample O that contains microparticles as a target 2 is made flow through a liquid feed pipe for measurement, a transmitted light obtained by irradiating the target 2 in the liquid feed pipe with measurement light is detected to capture transmission images, and the target 2 are, for example, measured and analyzed on the basis of the transmission images. Accordingly, the microparticle measuring device 1 includes a liquid feed pipe 10, light source units 20A and 20B, image capturing units 30A and 30B, and an analyzing unit 40.

The liquid feed pipe 10 is a pipe into which the liquid sample O containing the microparticles is fed to measure the microparticles. The liquid sample O containing the microparticles as the target 2 is supplied into the liquid feed pipe 10 via a pipe (not shown) connected to a sample pipe 5. The liquid feed pipe 10 has an inner diameter that is adjusted to cause the microparticles as the target 2 to be dispersed in the liquid sample. As a result, in the liquid feed pipe 10, the microparticles move one by one to a position between the light source units 20A and 20B and the image capturing units 30A and 30B. Consequently, it is possible for the microparticle measuring device 1 to measure individual microparticles in the liquid.

The material of the liquid feed pipe 10 is not particularly limited; for example, glass, resin, or the like is usable. The liquid feed pipe 10 needs to have light transmittance with respect to the measurement light.

Figure 2:
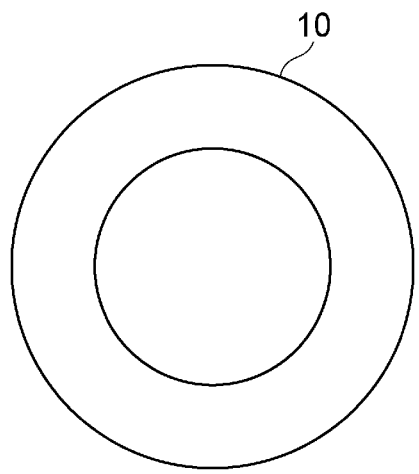
FIG. 2 is a conceptual diagram showing an example of a cross-sectional shape of a liquid feed pipe.
Figure 3:
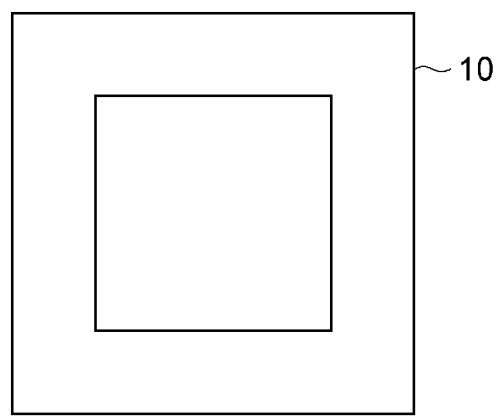
FIG. 3 is a conceptual diagram showing another example of the cross-sectional shape of the liquid feed pipe.

The cross-sectional shape (shape of a cross section perpendicular to a flowing direction) of the liquid feed pipe 10 is not particularly limited; for example, as shown in FIG. 2, the cross-sectional shape may be a shape surrounded by two concentric circles (annular shape) or, as shown in FIG. 3, the cross-sectional shape may be a shape surrounded by two squares. When the cross-sectional shape is the annular shape, it is basically possible for each of the image capturing units 30A and 30B, even when the direction of image capturing thereof in the cross section orthogonal to the flowing direction is changed, to capture an identical image regardless of the direction of image capturing. In contrast, when the cross-sectional shape is the shape surrounded by the two squares, it is possible for the image capturing units 30A and 30B, when being disposed so as to each face a flat portion of the liquid feed pipe 10, to capture transmission images that have been avoided from being subject to the influence of distortion generated when the measurement light or the transmitted light has passed through the liquid feed pipe 10.

During observation of the microparticles in the liquid feed pipe 10, the microparticles move in a flow passage in the liquid feed pipe 10, and therefore, the size (inner diameter) of the liquid feed pipe 10 is desirably small; however, to ensure the mechanical strength of the liquid feed pipe 10, the thickness of the liquid feed pipe 10 needs to be ensured. Thus, in the microparticle measuring device 1, the area of a region surrounded by the outer diameter of the liquid feed pipe 10 is preferably four to ten times the area of a gap portion configured such that through the inner portion, the liquid sample O passes in the cross section perpendicular to the flowing direction (moving direction of the liquid sample O) in the liquid feed pipe 10. However, the thickness of the liquid feed pipe 10 is preferably set in consideration of the sizes and the hardness (when the microparticles have high hardness, there is a possibility that the microparticles may damage the liquid feed pipe 10 by coming into contact with the liquid feed pipe 10 even at a low flow rate) of the microparticles, the flow rate of the liquid sample in the liquid feed pipe 10, and the like. Note that, in the cross section perpendicular to the flowing direction (moving direction of the liquid sample O) in the liquid feed pipe 10, when the area of the gap portion of the liquid feed pipe 10 is 1 to 100 times the cross-sectional area of a microparticle to be observed, focusing of the image capturing devices is easy during observation, and degradation of the transmission images of the liquid sample O is thus avoided.

The light source units 20A and 20B each irradiate a predetermined region of the liquid feed pipe 10 with the measurement light. A halogen lamp is usable as a light source of each of the light source units 20A and 20B. In addition, a SC light source that includes a seed light source and a nonlinear medium and that inputs light that is emitted by the seed light source into the nonlinear medium and outputs the light as supercontinuum (SC) light with a spectrum being spread over a broadband due to a nonlinear optical effect in the nonlinear medium is also usable as the light source of each of the light source units 20A and 20B. When the SC light source is used as the light source of each of the light source units 20A and 20B, it is possible to reduce influence on the target 2 because heating is reduced compared with the halogen lamp. Further, each of the light source units 20A and 20B may have an intensity modulating function.

It is preferable that the plurality of light source units 20A and 20B be provided, as shown in FIG. 1, and irradiate the liquid feed pipe 10 from angles different from each other in correspondence to the image capturing units 30A and 30B. Such an arrangement enables the image capturing units 30A and 30B to perform measurement with increased accuracy.

In the present embodiment, the wavelength of the measurement light emitted by each of the light source units 20A and 20B is not particularly limited and is selected, as appropriate, in accordance with the target 2 and the liquid around the target 2. Near infrared light is usable as the measurement light. Near infrared light is light of a wavelength band in a wavelength range of 800 nm to 2500 nm. Note that visible light is also usable as the measurement light. Visible light is light of a wavelength band in a wavelength range of 400 nm to 800 nm. In addition, near infrared light and visible light may be combined together to be used as the measurement light.

The image capturing units 30A and 30B each have a function of receiving the measurement light emitted by the light source units 20A and 20B and transmitted through the target 2 and detecting the intensity thereof. Therefore, the image capturing units 30A and 30B are disposed at positions respectively facing the light source units 20A and 20B with the liquid feed pipe 10 therebetween. The image capturing units 30A and 30B each include a detector in which a plurality of pixels are arranged in a two-dimensional form and each convert light received on the pixels into intensity information. Results of detection by the image capturing units 30A and 30B are sent to the analyzing unit 40.

The image capturing units 30A and 30B continuously capture the liquid sample that moves in the liquid feed pipe 10, thereby capturing the target 2 and all other components. In other words, instead of capturing the target 2 only, the image capturing units 30A and 30B capture the entire liquid sample in the liquid feed pipe 10. Then, from results of image capturing, the analyzing unit 40 distinguishes pixel information in which the target 2 is captured from pixel information in which the other components are captured, and, consequently, it is possible to obtain results of image capturing of the target 2. In other words, the image capturing units 30A and 30B obtain information for specifying the outer shape of the target 2 through image capturing. Further, the image capturing units 30A and 30B are capable of obtaining information on the shape (not limited to the outer shape, but including shapes such as concave and convex) of target 2 by changing image capturing conditions.

In addition, the image capturing units 30A and 30B preferably capture an identical image-capturing target, simultaneously. In other words, as shown in FIG. 1, the image capturing units 30A and 30B preferably capture images at an identical position in a view in the flowing direction of the liquid sample in the liquid feed pipe 10. As a result of such a configuration, it is possible to grasp, in directions different from each other, a state of the liquid sample that moves in the liquid feed pipe 10. While the liquid sample moves in the liquid feed pipe 10, solid bodies such as the target 2 may rotate, and thus, when the directions of image capturing are changed and images at positions different from each other in the flowing direction are captured, it may be impossible to sufficiently acquire information on the target 2. Therefore, the image capturing units 30A and 30B capture images at a specific position of the liquid feed pipe 10 to enables acquisition of more detailed information on the target 2.

The image capturing units 30A and 30B may detect only the intensity of, for example, light of a specific wavelength that enables distinguishing between the target 2 and the other components. In addition, the image capturing units 30A and 30B may detect an optical spectrum that includes intensity values of a plurality of wavelengths. The optical spectrum is a series of data containing intensity values that are each extracted for an optional wavelength from spectroscopic information and paired with the corresponding wavelength.

As the detector of each of the image capturing units 30A and 30B, for example, an MCT detector that contains mercury, cadmium, and tellurium, an InGaAs detector, or the like is usable. In addition, in a configuration in which the image capturing units 30A and 30B each detect the optical spectrum, each of the image capturing units 30A and 30B further includes, at the preceding stage of the detector, a spectrometer having a function of separating incident light according to wavelengths. As the spectrometer, for example, a wavelength selective filter, an interference optical system, a diffraction grating, or a prism is usable.

In addition, each of the image capturing units 30A and 30B may be a hyperspectral sensor that acquires a hyperspectral image. The hyperspectral image is an image in which one pixel is constituted by N number of pieces of wavelength data, the hyperspectral image containing, for each pixel, spectral information consisting of pieces of reflection intensity data corresponding to a plurality of wavelengths. In other words, having a feature of containing, for each pixel that constitutes the image, the pieces of intensity data corresponding to the plurality of wavelengths, the hyperspectral image is data of a three-dimensional structure including a two-dimensional element as an image and an element as spectral data. Note that, in the present description, hyperspectral image denotes an image that is constituted by pixels in which intensity data in at least four wavelength bands is contained per pixel.

The image capturing units 30A and 30B in which the optical spectrum is acquired after the transmitted light from the target 2 is separated is described above; however, the configuration of each of the image capturing units 30A and 30B for acquiring the optical spectrum is not limited thereto. For example, a configuration in which the wavelength of the light emitted by each of the light source units 20A and 20B is variable may be employed.

Each of the image capturing units 30A and 30B is preferably provided with a position adjusting mechanism capable of adjusting a distance between the image capturing unit 30A or 30B and the liquid feed pipe 10. It is possible to provide the position adjusting mechanism by providing a means for moving the image capturing units 30A and 30B along a rail; however, the specific configuration thereof is not particularly limited. Providing the position adjusting mechanism for changing the distance between the image capturing unit 30A or 30B and the liquid feed pipe 10 enables image capturing in which the liquid feed pipe 10 (target 2 inside thereof) is disposed at a position different from a focal point of each of the image capturing units 30A and 30B. Thus, when the liquid feed pipe 10 disposed at the position different from the focal points is captured by the image capturing units 30A and 30B, it is possible to capture an image, as the information on the target 2, containing information different from that as a result of capturing a target disposed typically at a focal point.

The position adjusting mechanism is preferably capable of moving at accuracy of 0.1 μm. As a result of such a configuration, it becomes possible to acquire more detailed information on the target 2. Note that the position adjusting mechanism may be disposed on the side of the liquid feed pipe 10; however, in order to enable the position adjusting mechanism to individually adjust a distance between each of the plurality of image capturing units and the liquid feed pipe 10, the position adjusting mechanism is preferably provided on the side of the image capturing units.

The analyzing unit 40 has a function of, for example, performing measurement, analysis, and the like of the target 2 by acquiring the results of image capturing of the target 2 sent from the image capturing units 30A and 30B and subjecting the results to operation processing. In addition, various determinations, evaluations, and the like may be performed on the basis of a result of measurement by the analyzing unit 40. For example, when the target 2 is cells, the analyzing unit 40 may determine whether the captured target 2 is cells of a specific type contained in the liquid sample or may identify differentiation degrees of the cells of the captured target 2. Thus, when the analyzing unit 40 performs determinations and evaluations of the target 2, previously providing the analyzing unit 40 with information that serves as standards for the determinations and the evaluations enables the determination and the evaluation to be performed by comparing the results of image capturing of the target 2 with the information that serves as the standards. In addition, the analyzing unit 40 may use a statistical technique, machine learning, or pattern recognition to perform the determination and evaluation of the target 2.

The analyzing unit 40 is a computer that includes a central processing unit (CPU), a random access memory (RAM), which is a main storage device, a read only memory (ROM), a communication module that communicates with other devices, and hardware such as an auxiliary storage device, for example, a hard disk. These constituent components operate to exhibit a function as the analyzing unit 40.

Next, a method of measurement by the microparticle measuring device 1 will be described. The measurement by the microparticle measuring device 1 includes a step in which the light source units 20A and 20B each irradiate, with the measurement light, the liquid sample that contains the target 2 and that moves in the liquid feed pipe 10, and the image capturing units 30A and 30B each detect transmitted light of the liquid sample, thereby capturing the target 2 or the other components of the liquid sample, a step in which the analyzing unit 40 measures and analyzes the target 2 on the basis of the results of image capturing by the image capturing units 30A and 30B, and a step in which results of the measurement and the analysis are output. Examples of the measurement and the analysis of the target 2 include, for example, specifying the number of the target 2 contained in the liquid sample from the results of image capturing, estimating the volume of the target 2, and, when the target 2 is cells, identifying the types of the cells, and identifying the differentiation degrees of the cells; however, the measurement and the analysis of the target 2 are not limited thereto.

In the microparticle measuring device 1, the image capturing units 30A and 30B are capable of acquiring transmission images of the target 2 in directions different from each other. Specifically, the image capturing units 30A and 30B capture, in the directions different from each other when viewed in the cross section perpendicular to the flowing direction (moving direction of the liquid sample O) in the liquid feed pipe 10, the transmitted light of the target 2. As a result of such a configuration, it is possible to grasp more detailed information on the target 2.

Figure 4:
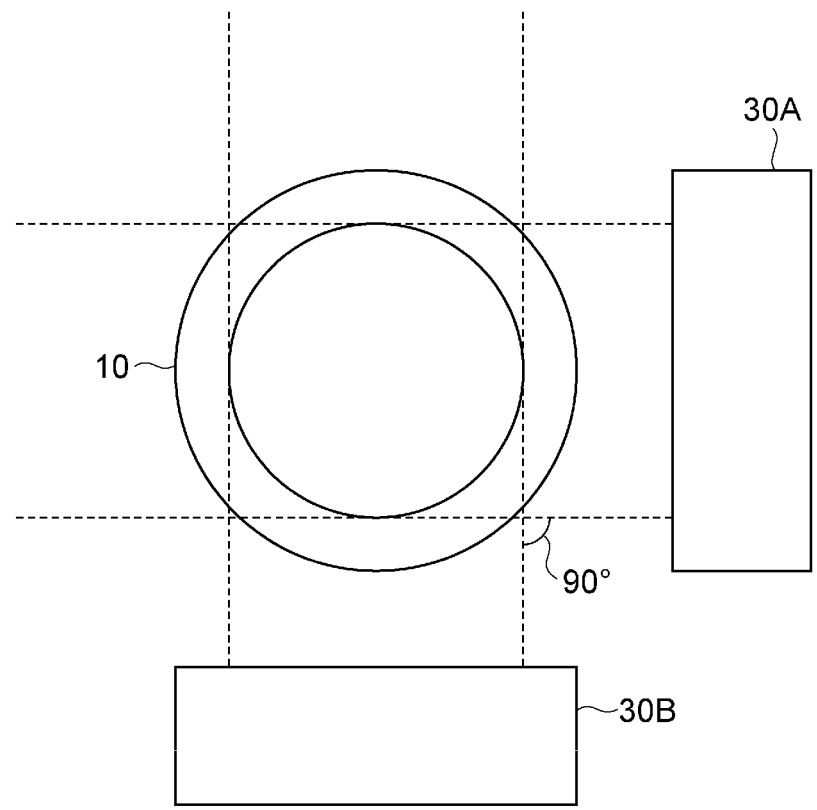
FIG. 4 is a conceptual diagram illustrating an arrangement of image capturing units.

More specifically, as shown in FIG. 4, directions of image capturing (directions of transmitted light incident on the image capturing units 30A and 30B) of the image capturing units 30A and 30B are preferably orthogonal to each other when viewed in the cross section perpendicular to the flowing direction (moving direction of the liquid sample O) in the liquid feed pipe 10. When such a configuration is employed, it becomes possible to uniformly capture the liquid sample and the target 2 that moves in the liquid feed pipe 10 by increasing each of regions captured by the image capturing units 30A and 30B so as to be larger than the inner diameter of the liquid feed pipe 10, as shown in FIG. 4. As a result, it becomes possible to acquire more detailed information on the target 2 from the results of image capturing by the image capturing units 30A and 30B, and it also becomes possible to analyze a target 2 with increased accuracy.

An angle between the directions of image capturing of the image capturing units 30A and 30B is preferably 60° or more when viewed in the cross section perpendicular to the flowing direction (moving direction of the liquid sample O) in the liquid feed pipe 10. When the angle between the directions of image capturing of the image capturing units 30A and 30B is 90°, it becomes possible to acquire more detailed information on the target 2, as described above; however, with the angle of 60° or more, it becomes possible to sufficiently, to some extent, acquire information for the measurement and the analysis of the target 2. The information for the measurement and the analysis of the target 2 is information to be used in the contents of the measurement and the analysis. For example, to estimate the volume of the target 2, three-dimensional information on the target 2 is needed in addition to two-dimensional information in one direction; accordingly, information on the three-dimensional structure of the target 2 serves as information for analysis and estimation.

As described above, according to the microparticle measuring device 1, transmission images of the microparticles are captured by the plurality of image capturing units 30A and 30B disposed in mutually different orientations with respect to the liquid feed pipe 10 when viewed in the cross section orthogonal to the moving direction of the liquid sample O in the liquid feed pipe 10, and the microparticles are analyzed on the basis of the transmission images. Thus, it becomes possible to analyze the microparticles with increased accuracy and without pretreatment such as bonding of labeled samples by capturing the transmission images of the microparticles in a plurality of directions and using the transmission images for the analysis.

In addition, it becomes possible to more clearly capture the transmission images of the microparticles by further including, similarly to the microparticle measuring device 1, the plurality of light source units 20A and 20B in correspondence to the plurality of image capturing units 30A and 30B, which enables the analysis of the microparticles to be performed with increased accuracy.

In addition, it becomes possible to acquire, as the transmission images, overall information on the microparticles by disposing the two image capturing units 30A and 30B such that the directions of image capturing thereof are orthogonal to each other when viewed in the cross section orthogonal to the moving direction of the liquid sample O in the liquid feed pipe 10, which enables the analysis of the microparticles to be performed with increased accuracy.

In addition, it becomes possible to capture the transmission images in a state, for example, in which the liquid feed pipe 10 is slightly shifted from the focal points of the image capturing unit 30A and the image capturing unit 30B by including the position adjusting mechanism capable of adjusting the distance between the image capturing unit 30A or the image capturing unit 30B and the liquid feed pipe 10, which enables information that is unacquirable through image capturing at the focal points to be acquired from the transmission images.

In addition, it becomes possible to more accurately acquire the transmission images of the microparticles by configuring such that the transmission images are captured at an identical position in the flowing direction of the liquid sample O in the liquid feed pipe 10 by the plurality of image capturing units 30A and 30B, which enables accuracy of analysis to be improved.

In addition, when employing a configuration in which information on the outer shape of the microparticles is acquired through image capturing by the image capturing units 30A and 30B, and the analyzing unit 40 estimates the volumes of the microparticles on the basis of the transmission images of the microparticles captured by the image capturing units 30A and 30B, it becomes possible to use the estimated volumes of the microparticles for the analysis of the microparticles.

In addition, when employing a configuration in which the analyzing unit 40 estimates the number of the microparticles from the transmission images of the microparticles acquired through image capturing by the image capturing units 30A and 30B, it becomes possible to use the estimated number of the microparticles for the analysis of the microparticles.

In addition, when employing a configuration in which information on the shapes of the microparticles is acquired through image capturing by the image capturing units 30A and 30B, and the analyzing unit 40 uses a statistical technique, machine learning, or pattern recognition to identify the microparticles, it becomes possible to analyze the microparticles by using the statistical technique, machine learning, or the pattern recognition.

In addition, when employing a configuration in which the transmission images of the microparticles are captured in a plurality of directions by using the aforementioned microparticle measuring device 1, and the analyzing unit uses the transmission images to determine whether the microparticles contained in the liquid sample O are cells of a specific type, it becomes possible to analyze the microparticles with increased accuracy.

In addition, when employing a configuration in which the transmission images of the microparticles are captured in a plurality of directions by using the aforementioned microparticle measuring device 1, and the analyzing unit uses the transmission images to estimate the differentiation degrees of cells, which are the microparticles contained in the liquid sample O, it becomes possible to analyze the microparticles with increased accuracy.

Note that the microparticle measuring device 1 and the microparticle analysis method according to the present invention are not limited by the aforementioned embodiment. For example, as an alternative to the configuration in the aforementioned embodiment in which the microparticle measuring device 1 includes the liquid feed pipe 10, the light source units 20A and 20B, the image capturing units 30A and 30B, and the analyzing unit 40, a configuration in which the light source units are omitted may be employed. In addition, three or more combinations of the light source unit and the image capturing unit may be included. In this case, when the image capturing units are disposed so as to be capable of capturing transmission images at an identical position in the flowing direction of the liquid sample in the liquid feed pipe, it becomes possible to acquire more detailed information on the microparticles in the liquid sample.

The invention claimed is:

1. A microparticle measuring device comprising:
a liquid feed pipe that has light transmittance and that has an inner portion configured such that through the inner portion, a liquid sample containing microparticles flows;
a plurality of image capturing units that are disposed in mutually different orientations with respect to the liquid feed pipe when viewed in a cross section orthogonal to a flowing direction of the liquid sample in the liquid feed pipe and that are configured to capture transmission images of the microparticles contained in the liquid sample that moves in the liquid feed pipe;
an analyzing unit that is configured to analyze the microparticles based on the transmission images of the microparticles captured by the image capturing units,
wherein the plurality of image capturing units are disposed so as to capture the transmission images at an identical position in a flowing direction of the liquid sample in the liquid feed pipe and are configured to acquire information on shapes of the microparticles.

2. The microparticle measuring device according to claim 1, further comprising
a plurality of light source units that are each disposed in an orientation facing a corresponding one of the plurality of image capturing units with the liquid feed pipe therebetween and that each is configured to emit measurement light toward the liquid feed pipe.

3. The microparticle measuring device according to claim 2, further comprising
a position adjusting mechanism capable of adjusting a distance between an image capturing unit included in the plurality of image capturing units and the liquid feed pipe.

4. The microparticle measuring device according to claim 3,
wherein two image capturing units of the plurality of image capturing units are disposed such that directions of image capturing thereof are orthogonal to each other when viewed in the cross section orthogonal to the flowing direction of the liquid sample in the liquid feed pipe.

5. The microparticle measuring device according to claim 2,
wherein two image capturing units of the plurality of image capturing units are disposed such that directions of image capturing thereof are orthogonal to each other when viewed in the cross section orthogonal to the flowing direction of the liquid sample in the liquid feed pipe.

6. The microparticle measuring device according to claim 1, further comprising
a position adjusting mechanism capable of adjusting a distance between an image capturing unit included in the plurality of image capturing units and the liquid feed pipe.

7. The microparticle measuring device according to claim 6,
wherein two image capturing units of the plurality of image capturing units are disposed such that directions of image capturing thereof are orthogonal to each other when viewed in the cross section orthogonal to the flowing direction of the liquid sample in the liquid feed pipe.

8. The microparticle measuring device according to claim 1,
wherein two image capturing units of the plurality of image capturing units are disposed such that directions of image capturing thereof are orthogonal to each other when viewed in the cross section orthogonal to the flowing direction of the liquid sample in the liquid feed pipe.

9. The microparticle measuring device according to claim 1,
wherein the shapes are outer shapes; and
wherein the analyzing unit is configured to estimate volumes of the microparticles based on the transmission images of the microparticles captured by the image capturing units.

10. The microparticle measuring device according to claim 1,
wherein the analyzing unit is configured to identify, based on the transmission images of the microparticles captured by the image capturing units, the microparticles by using a statistical technique, machine learning, or pattern recognition.

11. The microparticle measuring device according to claim 1,
   wherein the analyzing unit is configured estimate, based on the transmission images of the microparticles captured by the image capturing units, a number of the microparticles contained in the liquid sample.

12. A microparticle analysis method using the microparticle measuring device according to claim 1,
   wherein the analyzing unit is configured to determine whether the microparticles contained in the liquid sample are cells of a specific type.

13. A microparticle analysis method using the microparticle measuring device according to claim 1,
   wherein the analyzing unit is configured to evaluate differentiation degrees of cells, which are the microparticles contained in the liquid sample.

* * * * *